US007312058B2

(12) United States Patent
Kashiwagi et al.

(10) Patent No.: US 7,312,058 B2
(45) Date of Patent: Dec. 25, 2007

(54) MUTANT SERINE ACETYLTRANSFERASE (75) Inventors: Tatsuki Kashiwagi, Kawasaki (JP); Yuko Kai, Kawasaki (JP); Kohki Ishikawa, Kawasaki (JP); Ei-ichiro Suzuki, Kawasaki (JP); Hiroshi Takagi, Fukui (JP); Mikhail Kharisovich Ziyatdinov, Moscow (RU); Ekaterina Igorevna Redkina, Moscow (RU); Mikhail Markovich Gusyatiner, Moscow (RU)

(73) Assignee: Ajinomoto Co., Ltd., Tokyo (JP)

( * ) Notice: Subject to any disclaimer, the term of this patent is extended or adjusted under 35 U.S.C. 154(b) by 177 days.

(21) Appl. No.: 10/892,112

(22) Filed: Jul. 16, 2004

(65) Prior Publication Data
US 2005/0112731 A1 May 26, 2005

(30) Foreign Application Priority Data

Jul. 16, 2003 (RU) ............................. 2003121601
Dec. 5, 2003 (RU) ............................. 2003135291

(51) Int. Cl.
*C12N 9/10* (2006.01)
*C12N 1/12* (2006.01)
*C12N 15/74* (2006.01)
*C12P 13/12* (2006.01)
*C07H 21/00* (2006.01)

(52) U.S. Cl. .................. 435/193; 435/113; 435/252.1; 435/471; 536/23.1

(58) Field of Classification Search .................. None
See application file for complete search history.

(56) References Cited

U.S. PATENT DOCUMENTS

| | | | |
|---|---|---|---|
| 4,278,765 A | 7/1981 | Debabov et al. | ............ 435/172 |
| 5,661,012 A | 8/1997 | Sano et al. | ................ 435/115 |
| 6,040,160 A | 3/2000 | Kojima et al. | ............... 435/115 |
| 6,218,168 B1 * | 4/2001 | Leinfelder et al. | ........ 435/252.3 |
| 6,297,031 B1 | 10/2001 | Debabov et al. | ............ 435/115 |
| 6,653,111 B2 | 11/2003 | Debabov et al. | ............ 435/115 |
| 2003/0148473 A1 | 8/2003 | Livshits et al. | ............. 435/108 |

FOREIGN PATENT DOCUMENTS

| | | |
|---|---|---|
| JP | 56-018596 A | 2/1981 |
| JP | 11-155571 A | 6/1999 |
| JP | 11-299491 | 11/1999 |

OTHER PUBLICATIONS

Inoue et al., Eur J Biochem, 1999, 266: 220-227.*
Murillo et al., Cell Mol Biol Res, 1995, 41: 425-433, Abstract.*
Mino, K., et al., "Purification and Characterization of Serine Acetyltransferase from *Escherichia coli* Partially Truncated at the C-Terminal Region," Biosci. Biotechnol. Biochem. 1999; 63(1):168-179.
International Search Report for PCT Appl. No. PCT/JP2004/010216 (Aug. 31, 2004).
Denk D., et al., "L-Cysteine Biosynthesis in *Escherichia coli*: Nucleotide Sequence and Expression of the Serine Acetyltransferase (*cysE*) Gene from the Wild-type and a Cysteine-excreting Mutant", Journal of General Microbiology, vol. 133, pp. 515-525, (1987).
Nakamori S., et al., "Overproduction of L-Cysteine and L-Cystine by *Escherichia coli* Strains with a Genetically Altered Serine Acetyltransferase", Applied and Environmental Microbiology, vol. 64, No. 5, pp. 1607-1611 (1998).
Takagi H., et al., "PCR random mutagenesis into *Escherichia coli* serine acetyltransferase: isolation of the mutant enzymes that cause overproduction of L-cysteine and L-cystine due to the desensitization to feedback inhibition", FEBS Letters, vol. 452, pp. 323-327 (1999).
Mino, K., et al., "Increase in the Stability of Serine Acetyltransferase from *Escherihichia coli* against Cold Inactivation and Proteolysis by Forming a Bienzyme Complex", Biosci. Biotechnol. Biochem., vol. 65, No. 4, pp. 865-874 (2001).
Neidhardt F. C., et al., "*Escherichia coli* and *Salmonella*; Cellular and Molecullar Biology; Second Edition", ASM PRESS, American Society for Microbiology, 1325 Massachusetts Ave., Washington, D.C., pp. 514-527 (1996).
International Preliminary Report on Patentability for PCT Appl. No. PCT/JP2004/010216 (Jun. 1, 2006).

* cited by examiner

*Primary Examiner*—Joseph Woitach
*Assistant Examiner*—Ileana Popa
(74) *Attorney, Agent, or Firm*—Shelly Guest Cermak Cermak Kenealy & Vaidya LLP (57) ABSTRACT

O-acetylserine, L-cysteine and sulphurous compounds derived therefrom may be produced using a bacterium belonging to the genus *Escherichia* which harbors a mutant feedback-resistant serine acetyltransferases in which the amino acid sequence corresponding to positions from 89 to 96 in a wild-type serine acetyltransferase is replaced with any one of the amino acid sequences shown in SEQ ID NOS: 4 to 9, and feedback inhibition by L-cysteine in the bacterium is desensitized.

12 Claims, 5 Drawing Sheets

Figure 1. Construction of primers SEQ ID NO:18 and 19

5'-CGA TCC TC<u>G\* CAT G\*C\*</u>T TAA TTT C-3'  SEQ ID NO:18
        *Sph*I recognition site 5'-TAC AT<u>G CAT GC\*C</u> GTG TGA AGA ACT G-3'  SEQ ID NO:19
        *Sph*I recognition site The asterisk (\*) shows the location of mismatch

Figure 2

Top view

Side view

Pool of mutant *cysE* genes

Figure 5

MUTANT SERINE ACETYLTRANSFERASE

BACKGROUND OF THE INVENTION

1. Field of the Invention

The present invention relates to microbiological industry, and specifically relates to a method for producing amino acids. More specifically, the present invention concerns the use of a new feedback-resistant enzyme involved in cysteine biosynthesis. More specifically, the present invention concerns a new feedback-resistant mutant serine acetyltransferase, *E. coli* strains harboring the enzyme, and a method for producing L-cysteine by fermentation using the strains.

2. Description of the Related Art

Conventionally, L-amino acids have been industrially produced by fermentation methods utilizing strains of microorganisms obtained from natural sources or mutants of the said strains which have been specially modified to enhance L-amino acid productivity.

Many techniques to enhance L-amino acid productivity, for example, by transformation of microorganism with recombinant DNA (see, for example, U.S. Pat. No. 4,278,765) have been disclosed. These techniques are based on increasing the activity of the enzymes involved in amino acid biosynthesis and/or desensitizing the target enzymes from feedback inhibition by produced L-amino acid (see, for example, Japanese Laid-open application No 56-18596 (1981), WO 95/16042 or U.S. Pat. Nos. 5,661,012 and 6,040,160).

The biosynthesis of L-cysteine from L-serine in *E. coli* bacteria is performed by serine acetyltransferase, encoded by the cysE gene, and O-acetylserine (thiol)-lyase isozymes designated-A and -B, encoded by cysK and cysM genes. Serine acetyltransferase (also called "SAT"; EC 2.3.1.30) catalyzes the formation of O-acetyl-L-serine from acetyl-CoA and L-serine and plays a regulatory role in the biosynthesis of cysteine via feedback inhibition by L-cysteine (*Escherichia coli* and *Salmonella*, Second Edition, Editor in Chief: F. C. Neidhardt, ASM Press, Washington D.C., 1996).

A mutant of SAT from *Escherichia coli* without feedback sensitivity to L-cysteine, and wild-type SAT were isolated by Denk D. and Bock A. (J. Gen. Microbiol., 1987, 133 (Pt 3), 515-25). The mutant cysE gene showed a single base change in position 767 resulting in a substitution of methionine at position 256 to isoleucine. This mutant excreted L-cysteine.

Either replacement of wild-type Met-256 with 19 other amino acid residues in *E. coli* SAT encoded by cysE gene or introduction of a termination codon to truncate 256-273 C-terminal region leads, in most cases, to feedback resistant (fbr) phenotype The mutant SAT proteins, however, do not restore the level of activity of wild-type SAT (Nakamori S. et al, Appl. Environ. Microbiol., 1998, 64, 5, 1607-1611, WO 97/15673). Strains harboring a plasmid having these altered cysE genes produced up to 200 mg/l of cysteine, including cystine.

Numerous feedback-insensitive mutant SATs from *E. coli* were obtained by PCR via random mutagenesis. Mutations were identified along the entire amino acid sequence of SAT, but all the mutant SATs demonstrated a significantly decreased specific activity level (Takagi, H. et al, FEBS Lett., 1999, 452, 323-327).

The essential role of the C-terminal region of the SAT in the feedback inhibition by L-cysteine was also shown by Mino K. et al (Biosci. Biotechnol. Biochem. 1999, 63, 1, 168-179). The truncated SAT, which is the wild type SAT cleaved between Ser 253 and Met 254, resulting in a deletion of 20 amino acid residues from the C-terminus, was much less sensitive to feedback inhibition than the wild-type SAT.

It has also been reported that L-cysteine can be produced by a bacterial strain belonging to the genus *Escherichia*, characterized by both a suppressed L-cysteine decomposition system, e.g. a lower activity of cysteine desulfhydrase, and the retention of SAT having decreased feedback inhibition by L-cysteine, e.g. a mutant SAT with the 256$^{th}$ methionine at position 256 in the wild-type SAT substituted with another amino acid residue (JP11155571A2).

A recombinant serine acetyltransferase having a mutation in the sequence region of amino acids 97-100, 164-169, 237, 239-240, 245-259 and 267-269 or a deletion in the C-terminal sequence region of amino acids 237-240, 245-259 and 267-269 exhibits reduced sensitivity to L-cysteine in comparison to the wild-type enzyme, and is disclosed in US patent 6,218,168. The following mutations in SAT, encoded by double mutant cysEXIV allele, showed good resistance to cysteine ($K_i$>1000 µM) with relatively high activity (0.453 µM/min×mg): A to G at position 721, resulting in a change of Thr167 to Ala167 and ATG to TAG at positions 988-990, resulting in a stop-codon instead of Met256. Strain JM15, transformed with the cysEXIV allele, produced 2.3 g/l of L-cysteine after 48 hours of feed-batch fermentation process. The best yield of L-cysteine (3.9 g/l), however, was obtained using cysEDe1_255 mutant allele, whereby the 18 amino acids at the C-terminal region were truncated (U.S. Pat. No. 6,218,168).

As a rule, the fbr phenotype of an enzyme arises as a result of replacing one or more amino acid residues with other amino acid residues in protein sequence, and these replacements lead to reducing the enzyme activity.

The disadvantage of the mutant enzymes obtained by the methods described above, therefore, is the decreased activity of the mutant enzymes in comparison with the wild-type enzymes. Clearly there is a need in the art for maintainance of the mutant enzyme activity in the fbr phenotype.

SUMMARY OF THE INVENTION

An object of the present invention is to provide a mutant serine acetyltransferase having one or several mutations in the amino acid sequence at positions 89 to 96 of a wild-type serine acetyltransferase, and whereby feedback inhibition by L-cysteine is desensitized.

It is a further object of the present invention to provide the mutant serine acetyltransferase as described above, wherein the amino acid sequence corresponding to positions from 89 to 96 in a wild-type serine acetyltransferase is replaced with an amino acid sequence selected from the group consisting of SEQ ID NO: 4, 5, 6, 7, 8, and 9

It is a further object of the present invention to provide the mutant serine acetyltransferase as described above, wherein a wild type serine acetyltransferase is derived from *Escherichia coli;*

It is a further object of the present invention to provide the mutant serine acetyltransferase as described above, which includes deletion, substitution, insertion, or addition of one or several amino acids at one or a plurality of positions other than positions from 89 to 96, whereby substitutions of Asn to Lys at position 51, Arg to His at position 91 and His to Tyr at position 233 are excluded.

It is a further object of the present invention to provide a DNA encoding the mutant serine acetyltransferase as described above.

It is a further object of the present invention to provide a bacterium belonging to the genus *Escherichia*, which is transformed with the DNA as described above and has an ability to produce L-cysteine.

It is a further object of the present invention to provide a method for producing L-cysteine, which comprises cultivating the bacterium as described above in a culture medium and collecting from the culture medium the L-cysteine.

The SAT having any of fbr mutation as described above may be referred to as "the mutant SAT", a DNA coding for the mutant SAT may be referred to as "the mutant cysE gene", and a SAT without mutation may be referred to as "a wild type SAT".

DETAILED DESCRIPTION OF THE INVENTION

The present invention relates to the construction of mutant feedback resistant, high active enzymes which play a key role in biosynthesis of cysteine by *E. coli*. The present invention also relates to a procedure for synthesizing a large set of mutant cysE genes using the full randomization of cysE gene fragment.

Simultaneous substitution of amino acid residues in protein fragments where the fbr mutation is localized can produce mutant proteins which have an activity level close to the native level due to correct assessment of the three-dimension structure of enzyme.

The present invention will now be explained in further detail:

<1> Mutant SAT and Mutant cysE Gene

According to the three-dimensional SAT structure obtained by the inventors of the present invention, new regions of SAT essential for interaction with L-cysteine and responsible for SAT sensitivity to L-cysteine have been revealed (see Example 1).

The mutant SAT and mutant cysE gene of the present invention were obtained by randomized fragment-directed mutagenesis. Numerous mutations in cysE gene were obtained by randomization of a 24-nucleotide fragment of the cysE gene (see below). This fragment encodes the region from arginine at position 89 to asparagine at position 96 in the SAT protein sequence. Two neighboring amino acid residues were randomized at a time, so entire 89-96 region of the protein was randomized during 4 subsequent experiments.

Subsequent selection and screening of the recombinant clones having the mutant cysE genes, and then cloning the clones into expression vector allows selection of the fbr variants of the mutant SAT having different levels of biological activity, up to and including the activity level of derepressed wild-type (wt) SAT. As a wild-type SAT, the SAT from *E. coli* (EC-Number 2.3.1.30) is encompassed (SEQ ID NO:2).

The amino acid sequence of the mutant SAT having the fbr phenotype is encompassed by the present invention. The mutant SAT can be obtained by introducing mutations into a wild-type cysE gene using ordinary methods. The wild type cysE gene can be obtained by, for example, PCR (polymerase chain reaction; refer to White, T. J. et al., Trends Genet., 5, 185 (1989)) utilizing primers prepared based on the nucleotide sequence of the gene. As a wild type cysE gene, the cysE gene of *E. coli* is encompassed (nucleotide numbers 3779368 to 3780189 in the sequence of GenBank Accession NC_000913.1; gi:16127994). Genes encoding wild-type or mutant SAT from other microorganisms can be obtained in a similar manner. Introduction of mutations into the wild-type cysE gene can be performed by, for example, site-directed mutagenesis.

The amino acid sequence from positions 89 to 96 in the mutant SAT of the present invention contains one or several mutations. Preferably, the amino acid sequence of positions from 89 to 96 in the mutant SAT of the present invention is one of the sequences shown in SEQ ID NOS: 4 to 9. The corresponding amino acid sequence of mutant SAT of present invention, in which Val-95 and Asp-96 are replaced with Arg-95 and Pro-96, Gly-95 and Gly-96, or Leu-95 and Pro-96; Ala-94 is replaced with Thr-94; Arg-89 is replaced with Pro-89; Arg-89 and Thr-90 are replaced with Ser-89 and Leu-90; and the wild-type SAT of *E. coli* are illustrated in Table 1. Examples of the nucleotide sequences encoding these amino acid sequences are also shown in Table 1.

TABLE 1

| Allele of cysE gene | Sequence of randomized region of SAT protein (89→96 a.a.) | SEQ ID NO: | DNA sequence of randomized fragment of cysE gene (5'→3') | SEQ ID NO: |
|---|---|---|---|---|
| Wt | Arg Thr Arg Asp Pro Ala Val Asp | 3 | cgt acc cgc gac ccg gca gtc gat | 10 |
| CysE5 | Arg Thr Arg Asp Pro Ala <u>Arg Pro</u> | 4 | cgt acc cgc gac ccg gca AGA CCC | 11 |
| CysE12 | Arg Thr Arg Asp Pro Ala <u>Gly Gly</u> | 5 | cgt acc cgc gac ccg gca GGT GGT | 12 |
| CysE15 | Arg Thr Arg Asp Pro Ala <u>Leu Pro</u> | 6 | cgt acc cgc gac ccg gca CTA CCA | 13 |
| CysE1 | <u>Pro</u> Thr Arg Asp Pro Ala Val Asp | 7 | CCC acc cgc gac ccg gca gtc gat | 14 |
| CysE102 | Arg Thr Arg Asp Pro <u>Thr</u> Val Asp | 8 | cgt acc cgc gac cct ACA gtc gat | 15 |
| CysE142 | <u>Ser Leu</u> Arg Asp Pro Ala Val Asp | 9 | AGT CTA cgc gac ccg gca gtc gat | 16 |

The mutant SAT may include deletion, substitution, insertion, or addition of one or several amino acids at one or a plurality of positions other than 89$^{th}$ to 96$^{th}$, provided that the SAT activity is not deteriorated. The term "SAT activity" means activity to catalyze the reaction of the transfer of acetyl-group from acetyl-CoA to L-serine. Activity of SAT could be measured by a method described by, for example, Kredich, N. M. and Tomkins, G. M. (J. Biol. Chem. 1966, 241, 21, 4955-4965). The triple mutant with substitutions of Lys for the Asn at position 51, His for the Arg at position 91, and Tyr for the His at position 233 is excluded since it was earlier described by Takagi, H. et al (FEBS Left., 1999, 452, 323-327).

The number of "several" amino acids differs depending on the position of amino acid residues in the three dimensional structure of the protein and the type of the amino acids. This is because of the following reason. That is, some amino acids have high homology to one another and the difference in such an amino acid does not greatly affect the three dimensional structure of the protein. Therefore, the mutant SAT of the present invention may be one which has homology of not less than 30 to 50%, preferably 50 to 70%, more preferably 70 to 90%, most preferably not less than 90% with respect to the entire amino acid residues for constituting SAT, and which has the fbr SAT activity. Alternatively, the number of "several" amino acid residues referred to herein may be specifically between 2 to 20, preferably between 2 to 10, more preferably between 2 to 5.

In the present invention, "amino acid sequence corresponding to the sequence of positions from 89 to 96" means an amino acid sequence corresponding to the amino acid sequence of positions from 89 to 96 in the amino acid sequence of *E. coli* wild-type SAT. A position of amino acid residue may change. For example, if an amino acid residue is inserted at N-terminus portion, the amino acid residue inherently locates at the position 89 becomes position 90. In such a case, the amino acid residue at the position 90 is designated as the amino acid residue corresponding to the original position 89 in the present invention.

Therefore, changes to SAT such as those described above are typically conservative changes so as to maintain SAT activity. Substitution changes include those in which at least one residue in the amino acid sequence has been removed and a different residue inserted in its place. Examples of amino acids which may be substituted for an original amino acid in a SAT protein and which are regarded as conservative substitutions include: Ala substituted with ser or thr; arg substituted with gln, his, or lys; asn substituted with glu, gln, lys, his, asp; asp substituted with asn, glu, or gln; cys substituted with ser or ala; gln substituted with asn, glu, lys, his, asp, or arg; glu substituted with asn, gln, lys, or asp; gly substituted with pro; his substituted with asn, lys, gln, arg, tyr; ile substituted with leu, met, val, phe; leu substituted with ile, met, val, phe; lys substituted with asn, glu, gln, his, arg; met substituted with ile, leu, val, phe; phe substituted with trp, tyr, met, ile, or leu; ser substituted with thr, ala; thr substituted with ser or ala; trp substituted with phe, tyr; tyr substituted with his, phe, or trp; and val substituted with met, ile, leu.

DNA encoding substantially same protein as the mutant SAT as described above may be obtained, for example, by modifying the nucleotide sequence, for example, by means of the site-directed mutagenesis method so that one or more amino acid residues at a specified site are deleted, substituted, inserted, or added. DNA modified as described above may be obtained by conventionally known mutation treatments. Such mutation treatments include a method for treating a DNA containing the mutant cysE gene in vitro, for example, with hydroxylamine, and a method for treating a microorganism, for example, a bacterium, belonging to the genus *Escherichia* harboring the mutant cysE gene with ultraviolet irradiation or a mutating agent such as N-methyl-N'-nitro-N-nitrosoguanidine (NTG) and nitrous acid usually used for the such treatment.

The substitution, deletion, insertion, or addition of nucleotide as described above also includes mutation which occurs naturally (mutant or variant), for example, through random mutation, differences in species or genus of bacterium, which harbors SAT.

DNA encoding substantially the same protein as the mutant SAT can be obtained by isolating a DNA which hybridizes with the known cysE gene sequence (SEQ ID NO:1) or part of it as a probe under stringent conditions, and which encodes a protein having the SAT activity, from a cell harboring the mutant SAT which is subjected to mutation treatment.

The term "stringent conditions" include a condition under which so-called specific hybrid is formed, and non-specific hybrid is not formed. It is difficult to express this condition precisely by using any numerical value. However, for example, stringent conditions include conditions under which DNAs having high homology, for example, DNAs having homology of not less than 50% with each other hybridize, and DNAs having homology lower than the above with each other do not hybridize. Alternatively, the stringent conditions include a condition under which DNA's hybridize with each other at a salt concentration corresponding to ordinary conditions of washing in Southern hybridization, i.e., 60° C., 1×SSC, 0.1% SDS, preferably 0.1×SSC, 0.1% SDS.

Genes which will hybridize under conditions as described above includes genes having a stop codon generated within a coding region of the gene, and those having no activity due to mutation of active center. However, such inconveniences can be easily removed by ligating the gene with a commercially available expression vector, and investigating SAT activity of expressed protein.

<2> Bacterium Belonging to the Genus *Escherichia* of the Present Invention.

The bacterium of the present invention is a bacterium belonging to the genus *Escherichia* into which the mutant cysE gene described above is introduced. The term "a bacterium belonging to the genus *Escherichia*" means that the bacterium is classified as the genus *Escherichia* according to the classification known to a person skilled in the microbiology. An example of bacterium belonging to the genus *Escherichia* includes *E. coli*.

"Bacterium having an ability to produce L-cysteine" means a bacterium, which has an ability to cause accumulation of L-cysteine in a medium, when the bacterium of the present invention is cultured in the medium. The L-cysteine-producing ability may be imparted or enhanced by breeding. The term "bacterium having an ability to produce L-cysteine" used herein also means a bacterium, which is able to produce and cause accumulation of L-cysteine in a culture medium in amounts larger than a wild-type or parental strain. Examples of wild-type *E. coli* strain include *E. coli* strains MG1655 (ATCC47076, ATCC700926), K-12 and the like. The strain MG1655 is available from the American Type Culture Collection (10801 University Boulevard, Manassas, Va. 20110, United States of America).

The mutant cysE gene can be introduced by, for example, transformation of a bacterium belonging to the genus *Escherichia* with a recombinant DNA comprising a vector which functions in a bacterium belonging to the genus *Escherichia* and the mutant cysE gene. The mutant cysE gene can be also introduced by replacement of the cysE gene with the mutant cysE gene on a chromosome.

Examples of a suitable vector for introducing the mutant cysE gene include plasmid vectors such as pBR322, pMW118, pUC19 or the like, phage vectors such as 11059, IBF101, M13mp9 or the like and transposon such as Mu, Tn10, Tn5 or the like.

The introduction of a DNA into a bacterium belonging to the genus *Escherichia* can be performed, for example, by a method of D. A. Morrison (Methods in Enzymology, 68, 326 (1979)) or a method in which recipient bacterial cell are treated with calcium chloride to increase permeability of DNA (Mandel, M., and Higa, A., J. Mol. Biol., 53, 159, (1970)) and the like.

The amount of L-cysteine produced can be increased by introduction of the mutant cysE gene into an L-cysteine-producing bacterium belonging to the genus *Escherichia* as described above. Also, an ability to produce L-cysteine may be imparted to a bacterium into which the mutant cysE gene has been previously introduced.

Examples of the bacteria belonging to the genus *Escherichia* which have L-cysteine producing activity include *E. coli* strain JM15, which is transformed with different cysE alleles encoding feedback-resistant serine acetyltransferases (U.S. Pat. No. 6,218,168), *E. coli* strain W3110 having genes, which encode a protein suitable for secreting substances toxic for cells, overexpressed (U.S. Pat. No. 5,972, 663), *E. coli* strains having lowered cysteine desulfhydrase activity (JP11155571A2), and *E. coli* strain W3110 with increased activity of positive transcriptional regulator for cysteine regulon encoded cysB gene (PCT application WO0127307A1), and the like.

<3> Method of the Present Invention.

The method of present invention includes a method for producing L-cysteine, comprising the steps of cultivating the bacterium of the present invention in a culture medium, allowing the L-cysteine to be produced and, and collecting the L-cysteine from the accumulated L-cysteine from the culture medium.

In the present invention, the cultivation, collection and purification of L-cysteine from the medium and the like may be performed by conventional fermentation methods, wherein an amino acid is produced using a microorganism.

The culture medium employed in the present invention may be either a synthetic medium or a natural medium, so long as the medium includes a carbon source, a nitrogen source, a sulphur source and minerals and, if necessary, appropriate amounts of nutrients required for the growth of the microorganism.

The carbon source may include various carbohydrates such as glucose and sucrose, and various organic acids. Depending on the mode of assimilation of the used microorganism, alcohol including ethanol and glycerol may be used.

As the nitrogen source, various ammonium salts such as ammonia and ammonium salts, other nitrogen compounds such as amines, a natural nitrogen source such as peptone, soybean-hydrolysate and digested fermentative microorganism can be used. As the sulphur source, sulphates and thiosulphates can be used.

As minerals, potassium monophosphate, sodium chloride, calcium chloride, magnesium salts, ferrous salts, manganese salts and the like can be used.

Additional nutrients can be added to the medium, if necessary. For instance, if the microorganism requires methionine for growth (methionine auxotrophy) a sufficient amount of methionine can be added to the cultivation medium.

The cultivation is performed preferably under aerobic conditions such as by shaking, and stirring culture with aeration, at a temperature of 20 to 42° C., preferably 37 to 40° C. The pH of the culture is usually between 5 and 9, preferably between 6.5 and 7.2. The pH of the culture can be adjusted with ammonia, calcium carbonate, various acids, various bases, and buffers. Usually, an 1 to 5-day cultivation leads to the accumulation of the target L-amino acid in the liquid medium.

After cultivation, solids such as cells can be removed from the liquid medium by centrifugation or membrane filtration, and then the target L-amino acid can be collected and purified by ion-exchange, concentration and crystallization methods.

EXAMPLES

The present invention will be specifically explained with reference to the following non-limiting examples.

Example 1

Three-Dimensional Structure of SAT

Determination of three-dimensional structure of SAT was made as follows.

<1> Production and Purification of Selenomethionyl SAT

To produce the recombinant SAT in *Escherichia coli*, an expression plasmid for the cysE gene encoding SAT was constructed using vector pQE*. This vector was generated by modifying the *E. coli* expression vector pQE30 (Qiagen).

PCR was conducted using pQE30 as a template, and with oligonucleotide primers SEQ ID NO: 17 and 18. The primers were constructed based of the nucleotide sequence of vector pQE30 (www.qiagen.com). Primer SEQ ID NO:18 contains a SphI recognition site and the mismatches depicted in FIG. 1. A unique amplified band of 150 bp was digested with restriction enzymes XhoI and SphI to recover an 80 bp fragment of 80 bp. This fragment was ligated to the large fragment of pQE30 which had been previously digested with the same restriction enzymes. The resultant plasmid pQE* contains the SphI cleavage site at the initiation codon, instead of the sequence coding six consecutive His amino acid residues and the BamHI site.

The DNA fragment of the cysE gene was prepared by PCR with genomic DNA from *E. coli* DH5α and oligonucleotide primers SEQ ID NO:19 and 20 constructed on the basis of nucleotide sequence of cysE gene (the GenBank accession No. M15745). Primer SEQ ID NO:19 contains SphI recognition site and mismatch depicted in FIG. 1. Primer SEQ ID NO:20 contains HindIII recognition site in the 5'-end. The unique amplified band of 840 bp was digested with restriction enzymes SphI and HindIII and then ligated to the large fragment of pQE* which had been previously digested with the same restriction enzymes to construct plasmid pQE-SAT. As a result, a native serine residue coded by TCG triplet at position 2 in the recombinant SAT was replaced by proline coded by CCG triplet.

*E. coli* B834/DE3 cells (Novagen Co., USA) harboring the SAT expression plasmid pQE-SAT were cultivated at 37° C. for one night by LB medium [20g/l of bacto tryptone, 10 g/l of bacto yeast extract, 20 g/l of NaCl] with ampicillin (5 μg/ml). Subsequently, this seed culture was transferred to M9 medium [15.1 g/l of $Na_2HPO_4 \cdot 12H_2O$, 3 g/l of $KH_2PO_4$, 0.5 g/l of NaCl, 1 g/l of NH4Cl, 4 g/l of of 1M MgSO$_4$, 1 ml of 1M CaCl$_2$, 1 ml of FeCl$_3$ (3.5 mg/ml), 2.4 ml of thiamin (1 mg/ml)] with selenomethionine (40 µg/ml) and ampicillin (50 µg/ml). Cultivation was continued at 37° C. When the optical density at 560 nm reached at 0.6, 1 mM isopropyl-1-beta-D-galacto-pyranoside was added for the induction of selenomethionyl SAT expression. Cultivated cells were harvested by centrifugation.

The cell pellets were suspended in a solution of 50 mM Tris-HCl (tris(hydroxymethyl)aminomethane hydrochloride), 2 mM (±)-dithiothreitol, 5 mM EDTA-Na$_2$ (disodium ethylenediaminetetraacetate dihydrate) and were disrupted by ultrasonication. The supernatant was incubated for 10 minutes at 60° C. and cooled on ice for 10 minutes. Precipitates were removed by centrifugation. The solubilized selenomethionyl SAT solution was purified by ammonium sulfate precipitation and was dialyzed by a solution of 50 mM Tris-HCl, pH7.5, 2 mM (±)-dithiothreitol, and 5 mM EDTA-Na$_2$. Then it was applied to an anion-exchange column (ResourceQ 6 ml, Amersham Pharmacia Biotech, Tokyo, Japan) equilibrated with 50 mM Tris-HCl, pH7.5, 2 mM (±)-dithiothreitol and 5 mM EDTA-Na$_2$. After the column was washed with 1 column volume of the same buffer, the selenomethionyl SAT was eluted with a linear gradient of sodium chloride from 0 to 1 M over 10 column volumes, at a flow-rate of 6 ml/min. The eluted fractions were collected. After the addition of ammonium sulfate, the solution was applied to a hydrophobic-interaction chromatography column (HiPrep 16/10 Butyl; Amersham Pharmacia Biotech, Tokyo, Japan) equilibrated with 0.75 M ammonium sulfate, 50 mM Tris-HCl, pH7.5, 2 mM (±)-dithiothreitol and 5 mM EDTA-Na$_2$. After the column was washed with 1 column volume of the same buffer, the selenomethionyl SAT was eluted with a linear gradient of ammonium sulfate from 0.75 to 0 M over 10 column volumes, at a flow-rate of 5 ml/min. For buffer-exchange, the pooled fractions were dialyzed with a solution of 50 mM Tris-HCl, pH7.5, 2 mM (±)-dithiothreitol, 5 mM EDTA-Na$_2$.

<2> Crystallization

The crystallization of selenomethionyl SAT was performed. Cubical crystals were obtained which grew to a size (0.2×0.2×0.2 mm) sufficient for X-ray diffraction within about 5 days.

<3> Data Collection and Processing

The multiple-wavelength anomalous dispersion (MAD) data of the selenomethionyl SAT crystal were collected using the Quantam 4R CCD detector (ADSC), installed on the beam line 6B at the Photon Factory of the National Laboratory for High Energy Physics, Tsukuba, Japan. Before the collection of the X-ray diffraction data, an X-ray fluorescence spectrum was recorded and used to select the optimum wavelength for the MAD data collection. During the X-ray fluorescence spectrum measurement and the data collection, the selenomethionyl SAT crystal was flash-cooled at 95K after equilibration against a cryo-solvent containing 35 v/v % 2-methyl-2,4-pentanediol, 0.1M 2-(N-morpholino)ethanesulfonic acid—NaOH (pH6.2), and 1 mM L-cysteine. Data were collected at 0.9791 Å (the inflection point of the fluorescence spectrum, f'minimum), 0.9789 Å (f'maximum), 0.9500 Å (remote high-energy wavelength), and 1.0500 Å (remote low-energy wavelength). All four data sets were collected from the same crystal at a crystal-to-detector distance of 220 mm and using 1.0° oscillations per image. The diffraction data were processed using the programs DPS/MOSFLM (Rossman, M. G. and van Beek, C. G. (1999) Acta Crystallogr. Sect. D55, 1631-1640). The crystal of the selenomethionyl SAT diffracted up to 2.7 Å resolution. It belongs to the space group R3, with unit cell dimensions of a=101.2 Å, c=223.2 Å. The crystal contains four selenomethionyl SAT molecules (molecules A, B, C, and D) per asymmetric unit, with a solvent content of 35.3%.

<4> MAD Phasing and Phase Improvement

The MAD data were scaled together with the CCP4 (Beiley, S. (1994) Acta Crystallogr. Sect. D50, 760-763) program SCALEIT. Nineteen Se sites of 36 expected in the asymmetric unit were determined using the program SOLVE (Terwilliger, T. C., and Berendzen, J. (1996) Acta Crystallogr. Sect. D52, 743-748). Initial MAD phases were calculated with the program MLPHARE in CCP4. The final figure of merit value became 0.541 (40.0-2.7 Å resolution).

The MAD phases were improved using the program DM in CCP4. At first, the solvent flattening procedure was reiterated on the condition of 30% solvent content, using the 40.0-2.7 Å resolution data. Although the electron density map showed a relatively clear protein-solvent boundary, its quality was poor and difficult to interpret. The interpretation of the electron density map and the model building were performed using the program QUANTA (Accelrys Inc.) on an Octane graphics workstation (Silicon Graphics Inc.).

In the next step, the phases were further improved by the molecular averaging procedure. The non-crystallographic symmetry (NCS) parameters were initially determined by superimposing the positions of the Se atoms. Molecules A and B and molecules C and D were related by noncrystallographic 2-fold axes, respectively. Molecules A and C and molecules B and D were related by ½ translation along c-axis, respectively. The NCS parameters were refined during the molecular averaging procedure performed at 40.0-2.7 Å resolution. The molecular averaging procedure was successfully finished, yielding improved values for the mean figure of merit of combined phases (0.644) and the correlation coefficient (0.617→0.868). The map was improved and showed many secondary structures. The three-dimensional structure of the selenomethionyl SAT was constructed on this map.

<5> Three-Dimensional Structure of SAT

Figure 1:
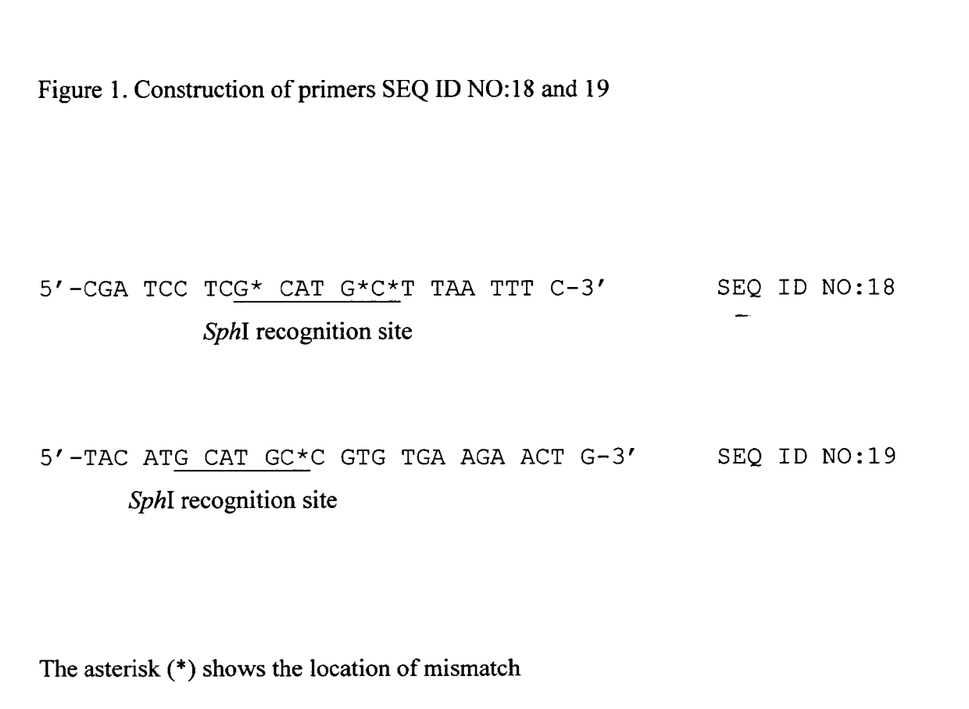
FIG. 1 shows construction of the primers SEQ ID NO:18 and 19.
Figure 2:
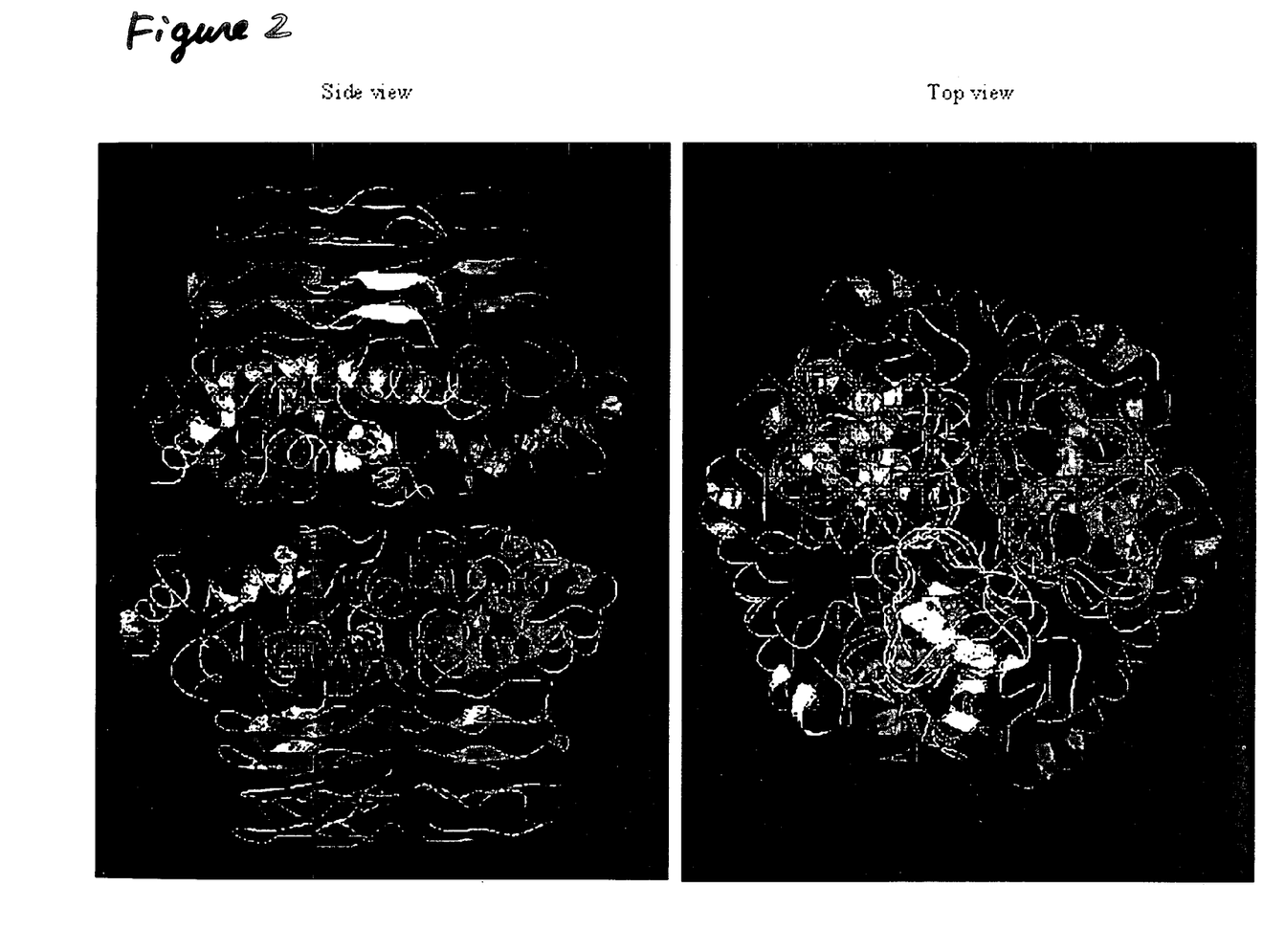
FIG. 2 shows the oligomeric structure of SAT.

FIG. 2 shows the oligomeric structure of SAT. As shown in FIG. 1, SAT forms a hexameric structure with 32-point symmetry. Three noncrystallographic 2-fold axis related dimers are related by the crystallographic 3-fold axis.

Figure 3:
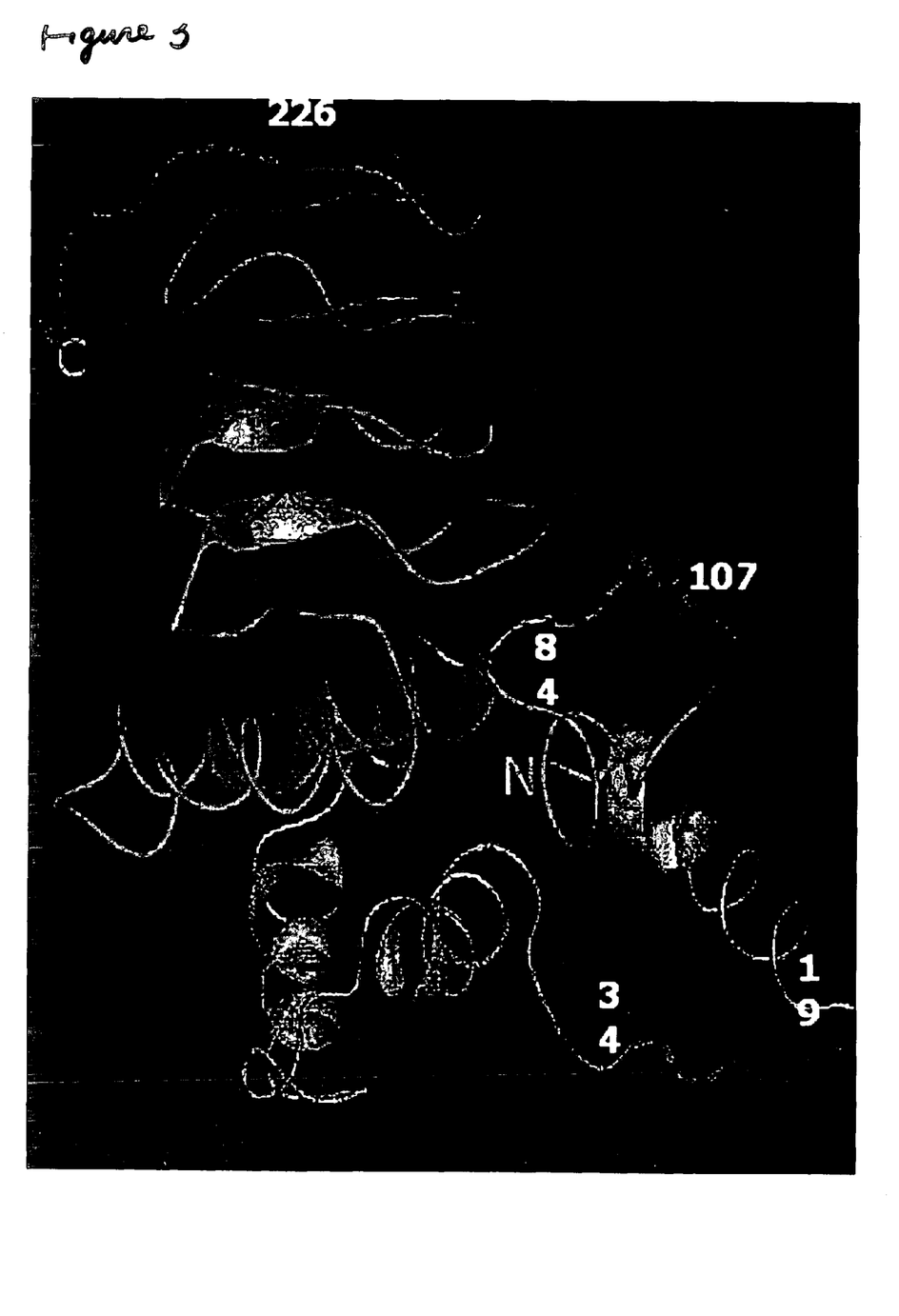
FIG. 3 demonstrates the three-dimensional structure of the SAT subunit.

FIG. 3 demonstrates the three-dimensional structure of SAT subunit. The SAT subunit is formed by two domains. An N-terminal domain contains many α-helices. The N-terminal domain helices in the SAT hexamer tightly interact with each other, and play an important role in the stabilization of the hexamer. The structure of a C-terminal domain is a left-handed parallel β helix domain (LβH). The LβH structure folds into a large coiled prism as if wound in a left-handed spiral around the surface of a prism. The faces of the LβH structure are formed by three flat parallel β-sheets. In the structure of the SAT hexamer, there are large clefts between the adjacent LβH structural domains, which are related by the crystallographic 3-fold axis. A lot of residues, which are responsible for the desensitization to feedback inhibition (Takagi, H. et al. (1999) FEBS Lett. 452, 323-327), are widely distributed in this cleft. Therefore, this cleft can be an essential region for the feedback inhibition. The region containing residues 89-9 also exists in this cleft, and therefore, was chosen for mutagenesis.

Example 2

Obtaining Mutant SATs having Region, Containing Residues 89-96, Randomized

<1> The Randomized Fragment-Directed Mutagenesis

At first, two plasmids pMW-P$_{ompC}$ and PMW-P$_{nlpD}$ were obtained.

The plasmid pMW-P$_{ompC}$ was obtained by cloning a 0.3 kb DNA fragment containing the promoter region of the ompC gene into the PaeI-SalI sites of the plasmid pMW118. The DNA fragment containing the ompC promoter was obtained by PCR using primers P4 (SEQ ID NO: 21) and P6 (SEQ ID NO: 22) and chromosomal DNA from E. coli strain MG1655 as a template. The ompC promoter region is used as a hybridization target for primer 4. An arbitrary sequence can substitute for the ompC promoter so long as primer P4 is designed to hybridize with the sequence.

The plasmid pMW-P$_{nlpD}$ was obtained by cloning a 0.3 kb DNA fragment containing the promoter region of the nlpD gene into the PaeI-SalI sites of the plasmid pMW118. The DNA fragment containing the nlpD promoter was obtained by PCR using primers P5 (SEQ ID NO: 23) and P7 (SEQ ID NO: 24) and chromosomal DNA from E. coli strain MG1655 as a template. The nlpD promoter region does not hybridize with the aforementioned primer. An arbitrary sequence can substitute for the nlpD promoter so long as primer P4 does not hybridize with the sequence.

Then whole wt cysE gene was obtained by PCR with primers: P1 (SEQ ID NO: 25) and P2 (SEQ ID NO: 26) using chromosomal DNA from E. coli strain MG1655 as a template. Obtained DNA fragment (0.83 kb) was cloned into SalI-XbaI sites of the plasmids pMW-P$_{ompC}$ and PMW-P$_{nlpD}$ resulting plasmids pMW-P$_{ompC}$-cysE and pMW-P$_{nlpD}$-cysE, respectively.

PyrobeSt™ DNA Polymerase used for PCR amplification was obtained from Takara Shuzo Co. (Japan) and is used under the conditions recommended by the supplier.

To construct the pool of mutant cysE genes with randomized positions 285 to 291, first, the fragment of cysE gene coding the sequence from 1$^{st}$ to 102$^{nd}$ amino acid residue of SAT was amplified by PCR. PCR was performed using plasmid pMW-P$_{ompC}$-cysE as the template and primer P3 (SEQ ID NO: 27), containing 6 nucleotides randomized and primer P4 (SEQ ID NO: 21) homologous to the sequence of promoter region of the ompC gene (see FIG. 1). The fixed 19-nucleotide 3'-end sequence of primer P3 is homologous to the sequence of cysE gene downstream Asp-96 codon and the fixed 20-nucleotide 5'-end is homologous to the sequence of cysE gene upstream Val-95. Also, primer P3 contains 6 random nucleotides depicted in the SEQ ID NO: 27 by letter "n". 20 ng of plasmid pMW-P$_{ompC}$-cysE were added as a template to PCR solution (50 µl) containing each of the two primers (10 pmol). Twenty five PCR cycles (96° C. for 0.4 min, 60° C. for 0.4 min, 72° C. for 1 min) was carried out with a model 2400 DNA thermal cycler (Perkin-Elmer Co., Foster City, Calif., USA). The 0.3 kb DNA fragment was obtained during 25 cycles of PCR.

At the second step, the 0.3 kbp DNA fragment obtained at the previous step was purified by agarose gel electrophoresis and used as a "primer" in a primer extension procedure to get the full sequence of cysE gene by 10 cycles of amplification (96° C. for 1 min, 40° C. for 1 min, 72° C. for 0.5 min). Plasmid pMW-P$_{nlpD}$-cysE was used as a template to prevent amplification of wild type cysE gene at the third step of PCR.

Figure 4:
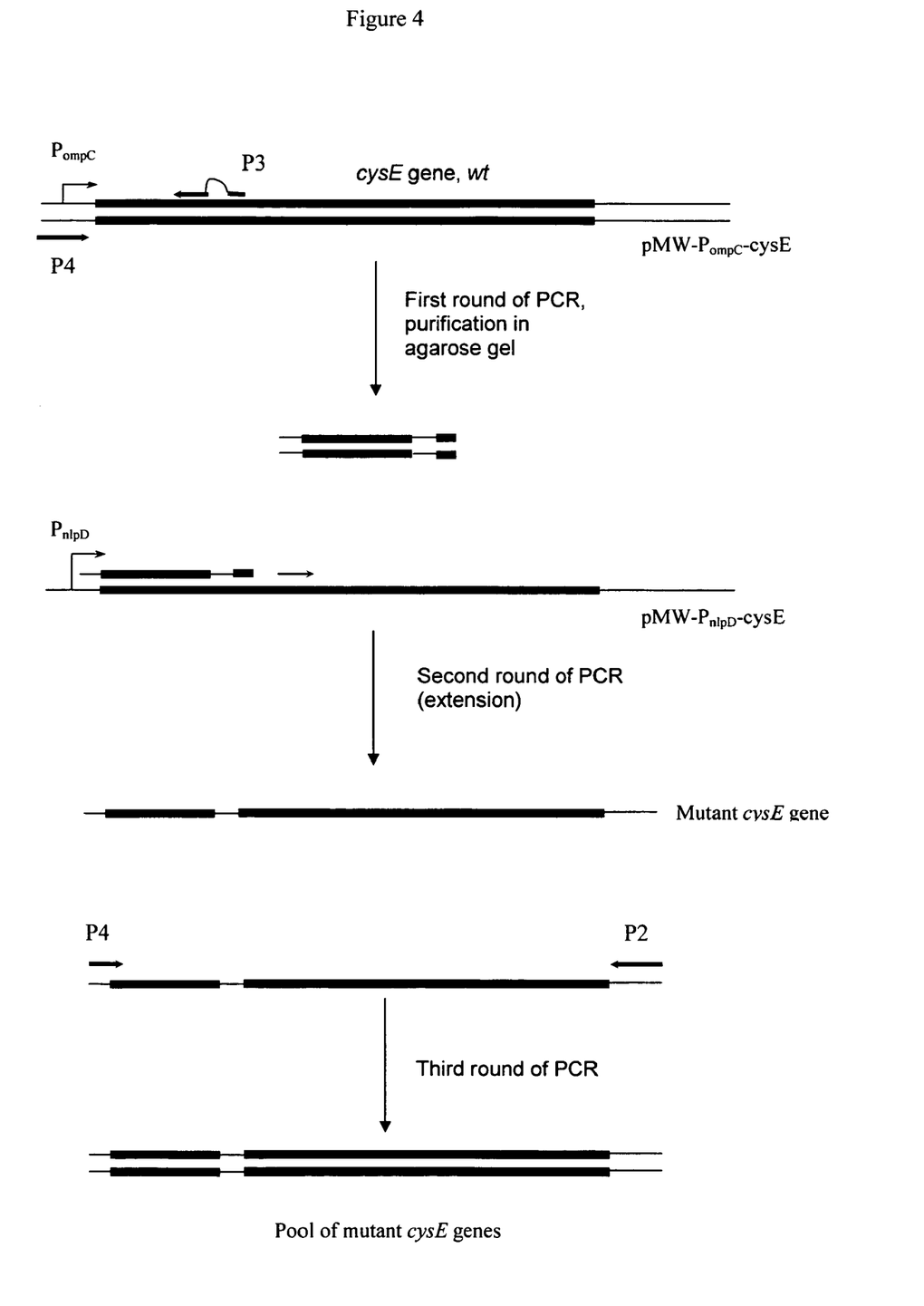
FIG. 4 shows the scheme for construction the pool of mutant cysE genes.

At the third step, the 10 µl aliquot of the reaction mixture was added to a fresh reaction mixture (40 µl) containing 50 pmol of primer P4 (SEQ ID NO: 21) homologous to the sequence of promoter region of the ompC gene (see FIG. 4), and primer P2 (SEQ ID NO: 26), and an additional 15 cycles (94° C. for 0.5 min, 57° C. for 0.5 min, 72° C. for 2 min) was performed.

0.83 kbp DNA fragment encoding pool of mutant cysE genes was purified by agarose gel electrophoresis, digested with SalI and XbaI, and then ligated to the pMW-P$_{ompC}$ vector digested with the same restriction enzymes.

About 100 ng of resulted plasmids pMW-P$_{ompC}$-cysE (random) was used for transformation of E. coli recipient cell.

<2> Isolation of New Mutant cysE Genes

E. coli strain LE392 cysE::Km$^R$ was used as a recipient strain for further experiments. The strain was obtained from E. coli strain LE392 (J. Sambrook et al., Molecular Cloning, 1989) by disruption of cysE gene. Disruption of cysE gene by introducing the kanamycin resistance gene was performed using strain JC7623 as described by Kushner, S. R., H. Nagaishi, and A. J. Clark. (Proc. Natl. Acad. Sci. USA, 1972, 69:1366-1370).

E. coli recipient strain LE392 cysE::Km$^R$ was transformed by the pool plasmids pMW-P$_{ompC}$-cysE(random). Mutant cysE genes encoding active SAT were selected by complementation of chromosome cysE mutation in the E. coli strain LE392 cysE::Km$^R$ on M9 agar plates supplied by 0.5% glucose and 50 mg/l methionine.

All obtained clones were tested for an ability to feed cysteine auxotrophs and about 15 variants were selected. The plasmids from these clones were purified and DNA sequences of structural part of cysE gene were determined by dideoxy chain termination method. To determine the SAT activity, the cysteine auxotroph, strain LE392 cysE::Km$^R$, was retransformed with these plasmids.

Mutant cysE gene (cysE256) having a single base change in position 767, resulting in replacement of methionine 256 with isoleucine (Denk D. and Bock A., J. Gen. Microbiol., 1987, 133 (Pt 3), 515-25), was obtained by the standard site-directed mutagenesis technique.

Example 3

Effect of Amino Acid Substitutions on Catalytic Property of SAT

Catalytic properties of mutant SATs were determined by the method described by Kredich, N. M. and Tomkins, G. M. (J. Biol. Chem., 1966, 241, 21, 4955-4965), which has been slightly modified. Acetyl coenzyme A and other chemicals used were from Sigma Chemical Co. (St. Louis, Mo., USA).

To determine the activity of mutant SAT, E. coli cells LE392 cysE::Km$^R$ carrying recombinant plasmids were grown in 5 ml of M9 medium up to the late exponential phase, washed with 0.14 M NaCl solution, and resuspended in 2 ml of buffer (pH 7.5, 50 mM potassium phosphate and 100 mM KCl). The cells were sonicated and the pellet was separated by centrifugation at 13000 rpm. The SAT-containing protein fractions in the resulting supernatant were precipitated by 5 volumes of saturated $(NH_4)_2SO_4$ and pellets were dissolved in 2 ml of buffer (pH 7.5, 50 mM potassium phosphate and 100 mM KCl). The obtained solution was added to 0.1 ml of reaction mixture (500 mM Tris-HCl (pH 8.5), 5 mM L-serine, 0.1 mM acetyl coenzyme A) and incubated at 37° C. for 10 min. The reaction was stopped by adding 0.3 ml of ethanol followed by centrifugation at 13000 rpm. 0.95 ml of 0.24 mM DTNB (5,5-dithio-bis-2-nitrobenzoate) solution was added to supernatant and mixture was incubated for 15 min. The SAT activity was assayed by measuring the absorbance at 412 nm. Obtained data are presented in Table 2 and FIG. 5.

TABLE 2

| cysE gene on the plasmid | Specific activity, relative units | Residual activity in presence 25 μM cysteine, % | Cysteine concentration of 50% inhibition ($I_{50}$), μM |
|---|---|---|---|
| cysE wild type | 2300 | 0 | 5 |
| cysE256 | 1400 | 88 | 120 |
| cysE5 | 900 | 100 | >700 |
| cysE12 | 600 | 95 | >700 |
| cysE15 | 480 | 100 | >700 |
| cysE1 | 400 | 93 | >700 |
| cysE102 | 650 | 85 | 130 |
| cysE142 | 2600 | 38 | 15 |

Figure 5:
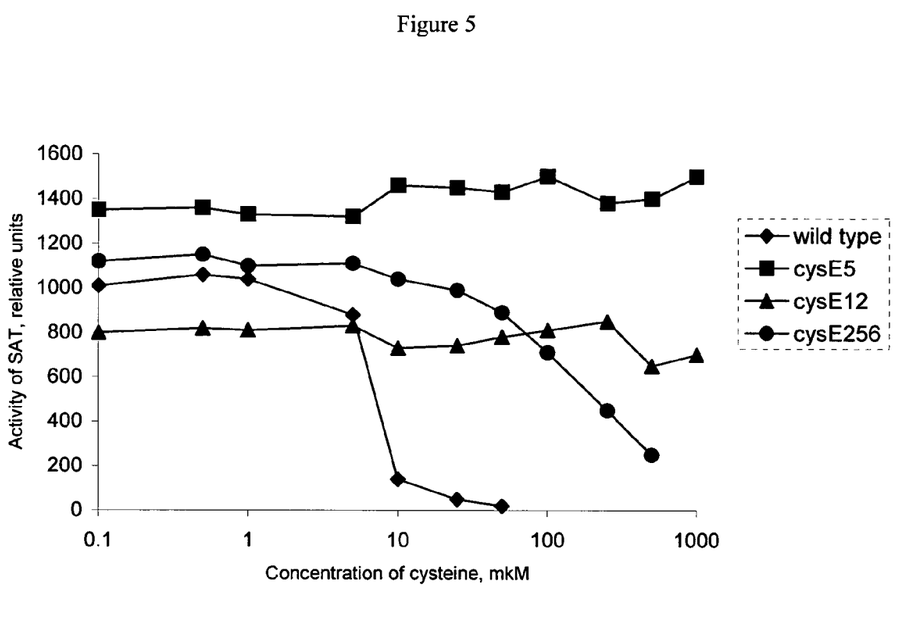
FIG. 5 shows catalytic properties of mutant SATs.

As it can be seen from data presented in Table 2 and FIG. 5, obtained mutants of the cysE gene, especially cysE5, cysE12, cysE15, and cysE1, encoding mutant SAT exhibited no sensitivity to feedback inhibition by L-cysteine. Such mutant SATs which are completely resistant to feedback inhibition by L-cysteine are useful for production of L-cysteine using L-cysteine producing bacteria.

Example 4

Effect of Enhanced Expression of Mutant cysE Gene on L-cysteine Production

The *E. coli* strain MG1655 (ATCC47076, ATCC700926) was used as a parental strain for evaluation of effect of enhanced expression of mutant cysE gene on L-cysteine production.

Plasmids pMW-P$_{ompC}$-cysEX (containing mutant cysEX gene encoding a mutant SAT in which Thr167 is replaced with Ala, which is described in the U.S. Pat. No. 6,218,168) and pMW-P$_{ompC}$-cysE5 were introduced into the *E. coli* strain MG1655. The resulting strains MG1655/pMW-P$_{ompC}$-cysEX and MG1655/pMW-P$_{ompC}$-cysE5 were cultivated overnight with shaking at 34° C. in 2 ml of nutrient broth supplemented with 100 mg/l of ampicillin. 0.2 ml of the obtained cultures were inoculated into 2 ml of a fermentation medium containing ampicillin (100 mg/l) in 20×200 mm test tubes, and cultivated at 34° C. for 42 hours with a rotary shaker at 250 rpm. The composition of the fermentation medium was the following: 15.0 g/l of $(NH_4)_2SO_4$, 1.5 g/l of $KH_2PO_4$, 1.0 g/l of $MgSO_4$, 20.0 g/l of $CaCO_3$, 0.1 mg/l of thiamine, 1% of LB, 4% of glucose, 300 mg/l of L-methionine and 0.5 g/l of $Na_2S_2O_3$.

After cultivation, the amount of L-cysteine which had accumulated in the medium was determined by the method described by Gaitonde, M. K. (Biochem. J., 104:2, 627-33 (1967)). Obtained data are presented in the Table 3.

TABLE 3

| Strains | Amount of L-cysteine, g/l |
|---|---|
| MG1655/pMW-P$_{ompC}$-cysEX | 0.27 |
| MG1655/pMW-P$_{ompC}$-cysE5 | 0.37 |

As it can be seen from Table 3, overexpression of the mutant cysE5 gene in the *E. coli* strain MG1655 improved cysteine productivity by the strain.

While the invention has been described in detail with reference to preferred embodiments thereof, it will be apparent to one skilled in the art that various changes can be made, and equivalents employed, without departing from the scope of the invention. All the cited references herein in their entirety, including the foreign priority documents, RU2003121601 and RU2003135291, are incorporated as a part of this application by reference.

SEQUENCE LISTING

```
<160> NUMBER OF SEQ ID NOS: 27

<210> SEQ ID NO 1
<211> LENGTH: 822
<212> TYPE: DNA
<213> ORGANISM: Escherichia coli
<220> FEATURE:
<221> NAME/KEY: CDS
<222> LOCATION: (1)..(822)

<400> SEQUENCE: 1 atg tcg tgt gaa gaa ctg gaa att gtc tgg aac aat att aaa gcc gaa      48
Met Ser Cys Glu Glu Leu Glu Ile Val Trp Asn Asn Ile Lys Ala Glu
1               5                   10                  15 gcc aga acg ctg gcg gac tgt gag cca atg ctg gcc agt ttt tac cac      96
Ala Arg Thr Leu Ala Asp Cys Glu Pro Met Leu Ala Ser Phe Tyr His
                20                  25                  30 gcg acg cta ctc aag cac gaa aac ctt ggc agt gca ctg agc tac atg      144
Ala Thr Leu Leu Lys His Glu Asn Leu Gly Ser Ala Leu Ser Tyr Met
            35                  40                  45 ctg gcg aac aag ctg tca tcg cca att atg cct gct att gct atc cgt      192
Leu Ala Asn Lys Leu Ser Ser Pro Ile Met Pro Ala Ile Ala Ile Arg
        50                  55                  60 gaa gtg gtg gaa gaa gcc tac gcc gct gac ccg gaa atg atc gcc tct      240
Glu Val Val Glu Glu Ala Tyr Ala Ala Asp Pro Glu Met Ile Ala Ser
```

```
                65                  70                  75                  80
gcg gcc tgt gat att cag gcg gtg cgt acc cgc gac ccg gca gtc gat      288
Ala Ala Cys Asp Ile Gln Ala Val Arg Thr Arg Asp Pro Ala Val Asp
             85                  90                  95 aaa tac tca acc ccg tta tta tac ctg aag ggt ttt cat gcc ttg cag      336
Lys Tyr Ser Thr Pro Leu Leu Tyr Leu Lys Gly Phe His Ala Leu Gln
                100                 105                 110 gcc tat cgc atc ggt cac tgg ttg tgg aat cag ggg cgt cgc gca ctg      384
Ala Tyr Arg Ile Gly His Trp Leu Trp Asn Gln Gly Arg Arg Ala Leu
            115                 120                 125 gca atc ttt ctg caa aac cag gtt tct gtg acg ttc cag gtc gat att      432
Ala Ile Phe Leu Gln Asn Gln Val Ser Val Thr Phe Gln Val Asp Ile
130                 135                 140 cac ccg gca gca aaa att ggt cgc ggt atc atg ctt gac cac gcg aca      480
His Pro Ala Ala Lys Ile Gly Arg Gly Ile Met Leu Asp His Ala Thr
145                 150                 155                 160 ggc atc gtc gtt ggt gaa acg gcg gtg att gaa aac gac gta tcg att      528
Gly Ile Val Val Gly Glu Thr Ala Val Ile Glu Asn Asp Val Ser Ile
                165                 170                 175 ctg caa tct gtg acg ctt ggc ggt acg ggt aaa tct ggt ggt gac cgt      576
Leu Gln Ser Val Thr Leu Gly Gly Thr Gly Lys Ser Gly Gly Asp Arg
            180                 185                 190 cac ccg aaa att cgt gaa ggt gtg atg att ggc gcg ggc gcg aaa atc      624
His Pro Lys Ile Arg Glu Gly Val Met Ile Gly Ala Gly Ala Lys Ile
        195                 200                 205 ctc ggc aat att gaa gtt ggg cgc ggc gcg aag att ggc gca ggt tcc      672
Leu Gly Asn Ile Glu Val Gly Arg Gly Ala Lys Ile Gly Ala Gly Ser
210                 215                 220 gtg gtg ctg caa ccg gtg ccg ccg cat acc acc gcc gct ggc gtt ccg      720
Val Val Leu Gln Pro Val Pro Pro His Thr Thr Ala Ala Gly Val Pro
225                 230                 235                 240 gct cgt att gtc ggt aaa cca gac agc gat aag cca tca atg gat atg      768
Ala Arg Ile Val Gly Lys Pro Asp Ser Asp Lys Pro Ser Met Asp Met
                245                 250                 255 gac cag cat ttc aac ggt att aac cat aca ttt gag tat ggg gat ggg      816
Asp Gln His Phe Asn Gly Ile Asn His Thr Phe Glu Tyr Gly Asp Gly
            260                 265                 270 atc taa                                                              822
Ile

<210> SEQ ID NO 2
<211> LENGTH: 273
<212> TYPE: PRT
<213> ORGANISM: Escherichia coli

<400> SEQUENCE: 2

Met Ser Cys Glu Glu Leu Glu Ile Val Trp Asn Asn Ile Lys Ala Glu
 1               5                   10                  15

Ala Arg Thr Leu Ala Asp Cys Glu Pro Met Leu Ala Ser Phe Tyr His
            20                  25                  30

Ala Thr Leu Leu Lys His Glu Asn Leu Gly Ser Ala Leu Ser Tyr Met
        35                  40                  45

Leu Ala Asn Lys Leu Ser Ser Pro Ile Met Pro Ala Ile Ala Ile Arg
    50                  55                  60

Glu Val Val Glu Glu Ala Tyr Ala Ala Asp Pro Glu Met Ile Ala Ser
65                  70                  75                  80

Ala Ala Cys Asp Ile Gln Ala Val Arg Thr Arg Asp Pro Ala Val Asp
                85                  90                  95
```

-continued

```
Lys Tyr Ser Thr Pro Leu Leu Tyr Leu Lys Gly Phe His Ala Leu Gln
            100                 105                 110

Ala Tyr Arg Ile Gly His Trp Leu Trp Asn Gln Gly Arg Arg Ala Leu
        115                 120                 125

Ala Ile Phe Leu Gln Asn Gln Val Ser Val Thr Phe Gln Val Asp Ile
    130                 135                 140

His Pro Ala Ala Lys Ile Gly Arg Gly Ile Met Leu Asp His Ala Thr
145                 150                 155                 160

Gly Ile Val Val Gly Glu Thr Ala Val Ile Glu Asn Asp Val Ser Ile
                165                 170                 175

Leu Gln Ser Val Thr Leu Gly Gly Thr Gly Lys Ser Gly Asp Arg
            180                 185                 190

His Pro Lys Ile Arg Glu Gly Val Met Ile Gly Ala Gly Ala Lys Ile
        195                 200                 205

Leu Gly Asn Ile Glu Val Gly Arg Gly Ala Lys Ile Gly Ala Gly Ser
    210                 215                 220

Val Val Leu Gln Pro Val Pro Pro His Thr Thr Ala Ala Gly Val Pro
225                 230                 235                 240

Ala Arg Ile Val Gly Lys Pro Asp Ser Asp Lys Pro Ser Met Asp Met
                245                 250                 255

Asp Gln His Phe Asn Gly Ile Asn His Thr Phe Glu Tyr Gly Asp Gly
            260                 265                 270

Ile

<210> SEQ ID NO 3
<211> LENGTH: 8
<212> TYPE: PRT
<213> ORGANISM: Escherichia coli

<400> SEQUENCE: 3

Arg Thr Arg Asp Pro Ala Val Asp
 1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: randomized
      region of SAT

<400> SEQUENCE: 4

Arg Thr Arg Asp Pro Ala Arg Pro
 1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: randomized
      region of SAT

<400> SEQUENCE: 5

Arg Thr Arg Asp Pro Ala Gly Gly
 1               5

<210> SEQ ID NO 6
<211> LENGTH: 8
<212> TYPE: PRT
<213> ORGANISM: Artificial Sequence
```

```
<220> FEATURE:
<223> OTHER INFORMATION: Description of Artificial Sequence: randomized
      region of SAT

<400> SEQUENCE: 6

Arg Thr Arg Asp Pro Ala Leu Pro
  1               5

<210> SEQ ID NO 7
<211> LENGTH: 8
<212> TYPE: PRT
<213> ORGANISM: Artificial Sequence
<220> FEATURE:
<223> OTHER

```
<211> LENGTH: 24
<212> TYPE: DNA
<213> ORGANISM: Artificial Sequence
<220> FEATURE:
<223> OTHER INFORMATION: Description of Artificial Sequence: randomized
      region of cysE gene

<400> SEQUENCE: 12
cgtacccgcg acccggcagg tggt                                             24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: randomized
      sequence of cysE gene

<400> SEQUENCE: 13
cgtacccgcg acccggcact acca                                             24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: randomized
      sequence of cysE gene

<400> SEQUENCE: 14
cccacccgcg acccggcagt cgat                                             24

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: randomized
      sequence of cysE gene

<400> SEQUENCE: 15
cgtacccgcg accctacagt cgat                                             24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: randomized
      sequence of cysE gene

<400> SEQUENCE: 16
agtctacgcg acccggcagt cgat                                             24

<210> SEQ ID NO 17
<211> LENGTH: 16
<212> TYPE: DNA
<213> ORGANISM: Artificial Sequence
<220> FEATURE:
<223> OTHER INFORMATION: Description of Artificial Sequence: primer

<400> SEQUENCE: 17
tatcacgagg cccttt                                                      16

<210> SEQ ID NO 18
<211> LENGTH: 22
<212> TYPE: DNA
```

```
<213> ORGANISM: Artificial Sequence
<220> FEATURE:
<223> OTHER INFORMATION: Description of Artificial Sequence: primer

<400> SEQUENCE: 18
cgatcctcgc atgcttaatt tc                                              22

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 19
tacatgcatg ccgtgtgaag aactg                                           25

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 20
gcccaagctt ttagatccca tccccat                                         27

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 21
agctgagcat gcgagtgaag gttttgtttt gac                                  33

<210> SEQ ID NO 22
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 22
agctgagtcg acaaccctct gttatatgcc ttta                                 34

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 23
agctgagcat gcttccaact gcgctaatga cgc                                  33

<210> SEQ ID NO 24
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 24
agctgagtcg accccccagga aaaattggtt aataac                              36
```

<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 25
agctgagtcg acatgtcgtg tgaagaactg gaa                                       33

<210> SEQ ID NO 26
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 26
agctgatcta gaatagatga ttacatcgca tcc                                       33

<210> SEQ ID NO 27
<211> LENGTH: 45
<212> TYPE: DNA
<213> ORGANISM: Artificial Sequence
<220> FEATURE:
<223> OTHER INFORMATION: Description of Artificial Sequence: primer with
      randomized region
<220> FEATURE:
<221> NAME/KEY: misc_feature
<222> LOCATION: (21)..(26)
<223> OTHER INFORMATION: n=randomized nucleotide

<400> SEQUENCE: 27
aacaacgggg ttgagtattt nnnnnntgcc gggtcgcggg tacgc                          45

What is claimed is:

1. A mutant serine acetyltransferase comprising an amino acid sequence selected from the group consisting of:
   a) SEQ. ID NO. 2, wherein the amino acid sequence thereof corresponding to positions from 89 to 96 contains one or several mutations,
   b) an amino acid sequence which is at least 90% homologous to SEQ ID NO. 2, wherein the amino acid sequence thereof corresponding to positions from 89 to 96 contains one or several mutations, and
   wherein said one or several mutations results in said mutant serine acetyltransferase being desensitized to feedback inhibition by L-cysteine,
   and wherein the triple mutant with substitutions of Lys for the Asn at position 51, His for the Arg at position 91 and Tyr for the His at position 233 is excluded.

2. The mutant serine acetyltransferase according to claim 1, wherein the amino acid sequence corresponding to positions from 89 to 96 is replaced with an amino acid sequence selected from the group consisting of SEQ ID NOs: 4, 5, 6, 7, 8, and 9.

3. The mutant serine acetyltransferase according to claim 1, which has the amino acid sequence of SEQ. ID NO. 2, wherein the amino acid sequence thereof corresponding to positions from 89 to 96 contains one or several mutations.

4. A DNA encoding the mutant serine acetyltransferase of claim 1.

5. A bacterium belonging to the genus *Escherichia*, which is transformed with the DNA of claim 4, and wherein said bacterium has an ability to produce L-cysteine.

6. A method for producing L-cysteine, which comprises cultivating the bacterium of claim 5 in a culture medium, and collecting the L-cysteine from the culture medium.

7. A DNA encoding the mutant serine acetyltransferase of claim 2.

8. A bacterium belonging to the genus *Escherichia*, which is transformed with the DNA according to claim 7, and wherein said bacterium has an ability to produce L-cysteine.

9. A method for producing L-cysteine, which comprises cultivating the bacterium of claim 8 in a culture medium, and collecting the L-cysteine from the culture medium.

10. A DNA encoding the mutant serine acetyltransferase of claim 3.

11. A bacterium belonging to the genus *Escherichia*, which is transformed with the DNA according to claim 10, and wherein said bacterium has an ability to produce L-cysteine.

12. A method for producing L-cysteine, which comprises cultivating the bacterium of claim 11 in a culture medium, and collecting the L-cysteine from the culture medium.

* * * * *

UNITED STATES PATENT AND TRADEMARK OFFICE
CERTIFICATE OF CORRECTION

PATENT NO. : 7,312,058 B2  Page 1 of 1
APPLICATION NO. : 10/892112
DATED : December 25, 2007
INVENTOR(S) : Kashiwagi et al.

It is certified that error appears in the above-identified patent and that said Letters Patent is hereby corrected as shown below:

Title page, item (73)

Assignee: should read as follows: Ajinomoto Co., Inc.

Signed and Sealed this

Thirteenth Day of May, 2008

JON W. DUDAS
*Director of the United States Patent and Trademark Office*